United States Patent [19]

Schubert

[11] Patent Number: 5,028,706
[45] Date of Patent: Jul. 2, 1991

[54] PROCESS FOR THE PREPARATION OF HALOSILANES

[75] Inventor: Hans H. Schubert, Frankfurt am Main, Fed. Rep. of Germany

[73] Assignee: Hoechst Aktiengesellschaft, Frankfurt am Main, Fed. Rep. of Germany

[21] Appl. No.: 379,094

[22] Filed: Jul. 13, 1989

[30] Foreign Application Priority Data

Jul. 15, 1988 [DE] Fed. Rep. of Germany ....... 3823979

[51] Int. Cl.$^5$ ............................................... C07F 7/12
[52] U.S. Cl. ..................................... 546/14; 556/474
[58] Field of Search ........................... 346/14; 536/474

[56] References Cited

PUBLICATIONS

Benkeser et al., "J. Am. Chem. Soc.", vol. 76 (1954), pp. 1252–1253.
Bazant et al., "Organosilicon Compounds", vol. 1, (1965), pp. 225–237 (Academic Press).

Primary Examiner—Robert T. Bond
Attorney, Agent, or Firm—Curtis, Morris & Safford

[57] ABSTRACT

The present invention relates to a process for the preparation of compounds of the formula I

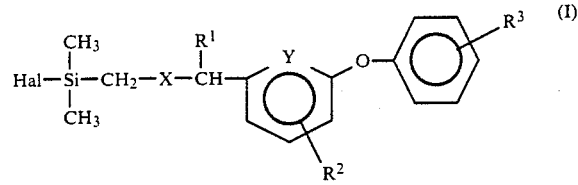

in which Hal denotes F, Cl, Br or I; X denoted O, S or $CH_2$; Y denotes CH or N; $R^1$ denotes H or ($C_1$–$C_4$-alkyl; $R^2$ denotes H, F, Cl or Br and $R^3$ denotes H, F, Cl, Br, ($C_1$–$C_4$)alkyl or ($C_1$–$C_4$)alkoxy, which comprises reacting a compound of the formula II

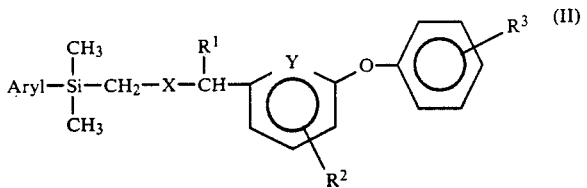

in which aryl stands for an unsubstituted or substituted phenyl, naphthyl or thienyl radical of the formulae (A), (B) or (C)

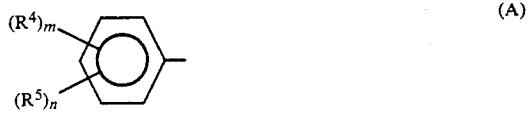

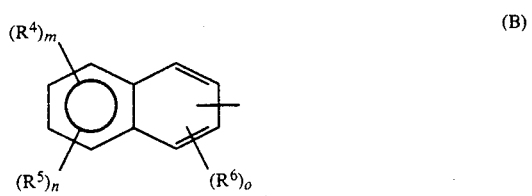

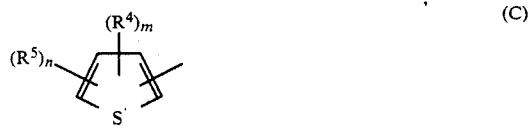

in which $R^4$, $R^5$ and $R^6$ independently of each other denote H, alkyl, alkoxy, alkylthio, dialkylamino, phenoxy, phenylthio or phenyl and m, n and o independently of each other denote the values 0, 1 or 2, and X, Y, $R^1$, $R^2$ and $R^3$ are as defined in formula I, with a halogen or a halogen compound of the formula III $Hal_p$—$Z_q$ (III)

in which Z denotes F, Cl, Br, I, H, $PHal_4$ or $SO_2Hal$ and p and q independently of each other denote the values 1 to 5 and Hal is as defined in formula I.

4 Claims, No Drawings

PROCESS FOR THE PREPARATION OF HALOSILANES

The object of the present invention is a process for the preparation of compounds of the formula I

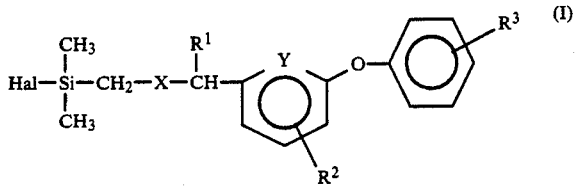

in which
Hal denotes F, Cl, Br or I,
X denotes O, S or $CH_2$,
Y denotes CH or N,
$R^1$ denotes H or $(C_1-C_4)$alkyl,
$R^2$ denotes H, F, Cl or Br and
$R^3$ denotes H, F, Cl, Br, $(C_1-C_4)$alkyl or $(C_1-C_4)$alkoxy,
which comprises reacting a compound of the formula II

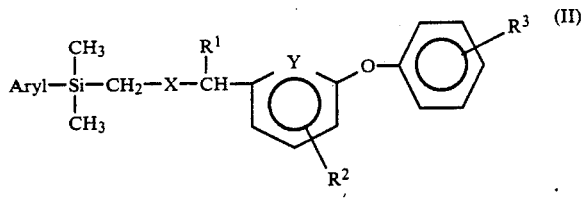

in which aryl stands for an unsubstituted or substituted phenyl, naphthyl or thienyl radical of the formulae (A), (B) or (C)

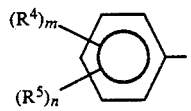

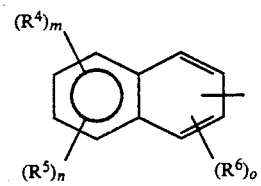

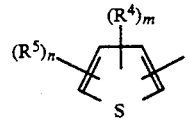

in which $R^4$, $R^5$ and $R^6$ independently of each other denote H, $(C_1-C_5)$-alkyl, $(C_1-C_5)$-alkoxy, $(C_1-C_5)$-alkylthio, di-$(C_1-C_4)$-alkylamino, phenoxy, phenyl or phenyl and m, n and o independently of each other denote the values 0, 1 or 2, and X, Y, $R^1$, $R^2$ and $R^3$ are as defined in formula I,
with a halogen or a halogen compound of the formula III $$Hal_p-Z_q \qquad (III)$$

in which Z denotes F, Cl, Br, I, H, $PHal_4$ or $SO_2Hal$ and p and q independently of each other denote the values 1 to 5 and Hal is as defined in formula I.

Preferred starting materials of the formula II have an unsubstituted, mono- or disubstituted phenyl radical of the formula A for aryl. Preferred halogenating agents of the formula III are those with p and q=1, such as, for example, halogens, in particular chlorine or bromine, anhydrous hydrogen halides and also sulfuryl halides and phosphorus(V) halides.

The compounds of the formula I and II are known and have significance as insecticidal, acaricidal or nematocidal active compounds (compounds of the formula II: EP-A-0,224,024) or their precursors (compounds of the formula I: EP-A-0,224,024, EP-A 0,249,015).

Processes for the preparation of these compounds are likewise described in these European Offenlegungsschriften. The processes for the preparation of the intermediates of the formula I described therein are in some cases very complicated in terms of process technology and do not lead to products of such a purity that these could be used directly for a further reaction. Since the compounds of the formula I can be converted very easily into derivatives of the compounds of the formula II, in which Si instead of aryl is substituted by a heterocyclic radical such as, for example, pyridyl (cf. exemplary embodiments 1 and 2), and these have particular significance as insecticidal or acaricidal active compounds, it was the object of the present invention to provide a process for the preparation of the compounds I which was simple in terms of process technology and, at the same time, selective.

Starting from the compounds of the formula II, the formation of the compounds of the formula I which occurred selectively and with good yields was particularly surprising in the process according to the invention. Whereas benzyl alkyl ethers and, in particular, benzyl alkyl sulfides are customarily halogenated in the benzylic position even under very mild conditions (see: H. Böhme and A. Dörries, Chem. Ber. 89, 723 (1956); H. Böhme and H. J. Gran, Liebigs Ann. Chem. 577, 68 (1952), the attack of the halogenating agent in the case of the starting materials of the formula II does not take place in the benzylic position, but selectively on the aryl silicon bond with formation of the halosilanes of the formula I easily accessible in this way. The best yields are thus achieved if the reaction is carried out in apolar to weakly polar aprotic solvents such as, for example, heptane, hexane, pentane, cyclohexane, benzene, halogenated benzenes, ethers, methylene chloride, chloroform or carbon tetrachloride, at temperatures from −78° C. to 80° C., the optimum temperature range and the solvent varying with the aryl radical to be removed and the halogenating agent employed. Whereas reactions of the starting materials II with chlorine occur even at temperatures from −70° C. to −10° C., the corresponding silyl iodides can preferably be obtained at temperatures from 0°-80° C. and with considerably longer reaction times. Electron-rich aryl radicals such as, for example, the p-anisyl radical are removed considerably more rapidly in these reactions at a given temperature than the unsubstituted phenyl radical. The choice of the solvent is made so that this can neither enter into side reactions with the halogenating agent III nor with the final products I. Thus, in reactions with chlorine, preferably tetrachloromethane or chlorinated benzene derivatives such as o-dichlorobenzene and the like, are employed as solvents. On the other hand, hydrogen chloride can also be used in ethereal solvents such as diethyl ether, THF, and ethylene glycol, diethylene glycol, triethylene glycol, tetraethylene glycol and polyethylene glycol dialkyl ethers.

1-1.1 molar equivalents, preferably 1-1.02 molar equivalents, of the halogenation agent are used per mole of the starting silane. Excesses employed if necessary are removed after conclusion of the reaction by addition of small amounts of a binder, for example an olefin such as cyclohexene.

The isolation of the desired products I is customarily carried out by distillation. However, the solutions of the silyl halides I obtained in this way are preferably used directly for silylation reactions. For this, it is necessary in some cases to exchange the solvent originally used for a diluent better suited to the subsequent reaction.

The process according to the invention is illustrated by the following examples:

EXEMPLARY EMBODIMENTS

1. Preparation and reaction of (bromo)(dimethyl)(3-phenoxybenzylthiomethyl)silane (I; Hal=Br, X=S, Y=CH, $R^1=R^2=R^3=H$).

4.1 g (10 mmol) of (dimethyl)(p-dimethylaminophenyl) (3-phenoxybenzylthiomethyl)silane are dissolved in 10 ml of anhydrous benzene and a solution of 1.6 g (10 mmol) of bromine in 5 ml of benzene is added dropwise with ice cooling.

The solution of the title compound thus obtained (yield: 76% of theory) is directly added dropwise at −70° C. to a solution of 2-ethoxy-5-lithiopyridine prepared from 2.1 g (10 mmol) of 5-bromo-2-ethoxypyridine and 4 ml of 2.5M n-butyllithium solution in 30 ml of THF. After warming to room temperature, the mixture is poured into 200 ml of ice-water and the product is extracted using heptane. The residue which remains on evaporating the extract is chromatographed on 110 g of silica gel using methylene chloride. 1.9 g (46%) of (2-ethoxypyrid-5-yl) (dimethyl)(3-phenoxybenzylthiomethyl)silane are obtained as a pale yellow oil.

2. Preparation and reaction of (bromo)(dimethyl)(3-phenoxybenzyloxymethyl)silane (I; Hal=Br, X=O, Y=CH, $R^1=R^2=R^3=H$).

5.9 g (15 mmol) of (dimethyl)(p-phenetyl)(3-phenoxybenzyloxymethyl)silane are dissolved in 10 ml of anhydrous benzene and a solution of 2.6 g (16.3 mmol) of bromine in 10 ml of benzene is added dropwise at 0°-6° C. After completion of the addition, the mixture is stirred for a further 5 min and the excess halogen is then destroyed by addition of 15 drops of cyclohexene.

The silyl bromide solution thus obtained (yield: 86% of theory) is added dropwise at −70° C. to −60° C. to the THF solution of 2-ethylthio-5-lithiopyridine prepared, as is customary, from 3.3 g (15 mmol) of 5-bromo-2-ethylthiopyridine and butyllithium solution. The same work-up as in Example 1 yields 4.3 g (70 %) of (2-ethylthiopyrid-5-yl)(dimethyl)(3-phenoxybenzyloxymethyl)silane as a pale yellow oil.

I claim:

1. A process for the preparation of compounds of the formula I

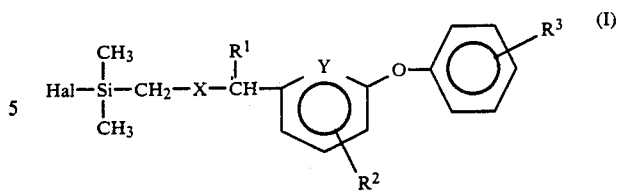

in which
Hal denotes F, Cl, Br or I,
X denotes O, S or $CH_2$,
Y denotes CH or N,
$R^1$ denotes H or $(C_1-C_4)$alkyl,
$R^2$ denotes H, F, Cl or Br and
$R^3$ denotes H, F, Cl, Br, $(C_1-C_4)$alkyl or $(C_1-C_4)$alkoxy, which comprises reacting a compound of the formula II

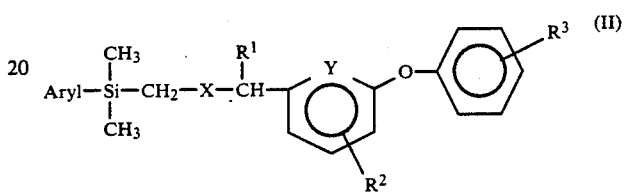

in which aryl stands for an unsubstituted or substituted phenyl, naphthyl or thienyl radical of the formulae (A), (B) or (C)

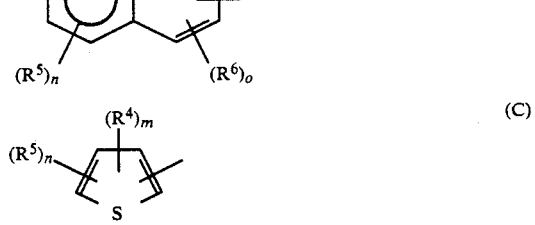

in which $R^4$, $R^5$ and $R^6$ independently of each other denote H, $(C_1-C_5)$-alkyl, $(C_1-C_5)$-alkoxy, $(C_1-C_5)$-alkylthio, di-$(C_1C_4)$-alkylamino, phenoxy, phenylthio or phenyl and m, n and o independently of each other denote the values 0, 1 or 2, and X, Y, $R^1$, $R^2$ and $R^3$ are as defined in formula I,
with a halogen or a halogen compound of the formula III

$Hal_p-Z_q$    (III)

in which Z denotes F, Cl, Br, I, H, $PHal_4$ or $SO_2Hal$ and p and q independently of each other denote the values 1 to 5 and Hal is as defined in formula I.

2. The process as claimed in claim 1, wherein the compound of the formula II is reacted with the compound of the formula III at temperatures between −78° C. and 80° C.

3. The process as claimed in claim 1, wherein the compound of the formula II is reacted with the compound of the formula III at temperatures between 0° C. and 80° C.

4. The process as claimed in claim 1, wherein the reaction is carried out in benzene as a solvent.

* * * * *